(12) United States Patent
Ulrich et al.

(10) Patent No.: US 7,167,251 B1
(45) Date of Patent: Jan. 23, 2007

(54) METHOD OF PROCESSING AN OPTICAL SUBSTRATE

(75) Inventors: Wilhelm Ulrich, Aalen (DE); Bernd Doerband, Aalen (DE); Rudolf Tannert, Aalen (DE)

(73) Assignee: Carl Zeiss SMT AG (DE)

( * ) Notice: Subject to any disclaimer, the term of this patent is extended or adjusted under 35 U.S.C. 154(b) by 0 days.

(21) Appl. No.: 11/230,455

(22) Filed: Sep. 21, 2005

Related U.S. Application Data (63) Continuation of application No. 10/845,259, filed on May 14, 2004, now abandoned.

(51) Int. Cl.
*G01B 11/02* (2006.01)

(52) U.S. Cl. ..................................... 356/512

(58) Field of Classification Search ............... 356/511, 356/512, 515, 517
See application file for complete search history.

(56) References Cited

U.S. PATENT DOCUMENTS

| | | | |
|---|---|---|---|
| 4,340,306 A | 7/1982 | Balasubramanian | |
| 4,732,483 A | 3/1988 | Biegen | |
| 5,361,312 A | 11/1994 | Kuchel | |
| 5,473,434 A | 12/1995 | de Groot | |
| 5,488,477 A | 1/1996 | de Groot | |
| 5,500,767 A * | 3/1996 | Maruyama et al. | 359/642 |
| 5,777,741 A | 7/1998 | Deck | |
| 5,982,490 A | 11/1999 | Ichikawa et al. | |
| 6,714,308 B1 * | 3/2004 | Evans et al. | 356/513 |
| 6,801,323 B1 * | 10/2004 | Evans | 356/513 |
| 2002/0063867 A1 | 5/2002 | Otto | |

OTHER PUBLICATIONS

J.E. Greivenkamp, et al., "Phase Shifting Interferometry", Optical Shop Testing, Second Edition, Edited by Daniel Malacara, Chapter 14.1 to 14.3, 1992, pp. 501-507.

* cited by examiner

*Primary Examiner*—Hwa (Andrew) Lee
*Assistant Examiner*—Michael A. Lyons
(74) *Attorney, Agent, or Firm*—Jones Day (57) ABSTRACT

A method of processing an optical substrate having a convex surface comprises an interferometric measurement using a beam of diverging measuring light traversing the substrate and reflected from a concave mirror.

22 Claims, 7 Drawing Sheets

Fig. 10 tion Ser. No. 10/845,259 filed May 14, 2004, now abandoned the entire contents of which are incorporated herein by reference.

BACKGROUND OF THE INVENTION

1. Field of the Invention

The present invention relates to the field of measuring and manufacturing optical surfaces. In particular the invention relates to an interferometer apparatus for measuring an optical surface and/or a method for qualifying the optical surface by using the apparatus and/or a method for manufacturing an optical substrate having the optical surface by using the interferometer apparatus.

2. Brief Description of Related Art

The substrate having the optical surface is, for example, an optical component such as an optical lens or an optical mirror used in optical systems, such as telescopes used in astronomy, or systems used for imaging structures of a mask ("reticle") onto a radiation sensitive substrate ("resist") in a lithographic method. The success of such an optical system is substantially determined by the precision with which the optical surface can be machined or manufactured to have a target shape. In such manufacture it is necessary to compare the shape of the machined optical surface with its target shape, and to determine differences between the machined and target surfaces. The optical surface is then further machined at those portions where differences between the machined and target surfaces exceed e.g. a predefined threshold.

Interferometric apparatuses are commonly used for high precision measurements of optical surfaces. Examples of such apparatus are disclosed in U.S. Pat. No. 4,732,483, U.S. Pat. No. 4,340,306, U.S. Pat. No. 5,473,434, U.S. Pat. No. 5,777,741, U.S. Pat. No. 5,488,477, which documents are incorporated herein by reference.

A conventional instrument and method for qualifying a convex optical surface will be illustrated with referenced FIG. 1 below. An interferometer apparatus 1 is of a Fizeau interferometer type having an optical axis 3 and a laser light source 5, such as a Helium-Neon-gas laser, emitting a laser beam 7. A microobjective 9 collimates laser beam 7 onto a pinhole of a spatial filter 11 such that a diverging beam 13 originates from the pinhole of spatial filter 11. A collimating lens 15 or a similar arrangement of plural lenses collimates diverging beam 13 to form a parallel beam 17. Wavefronts in parallel beam 17 are substantially flat wavefronts. A collimating lens 19 or similar collimating arrangement of plural lenses transforms parallel beam 17 into a converging beam 21 such that a crossover of converging beam 21 is formed in a region 23 on optical axis 3. Wavefronts in converging beam 21 are substantially spherical wavefronts.

A concave surface 25 of focussing lens 90 forms a reference surface or Fizeau surface of Fizeau interferometer 1. Concave surface 25 has a substantially spherical shape with crossover 23 coinciding with its center. Surface 25 is partially reflective, and spherical wavefronts of converging beam 21 are partially reflected from surface 25 such that they travel back in the beam path of interferometer 1 and are transformed to substantially flat wavefronts by focussing lens arrangement 19. A partially transmissive mirror 27 is arranged in the beam path of diverging beam 13 such that wavefronts reflected from reference surface 25 are imaged by a camera lens 29 onto a light sensitive substrate of a camera 31.

An optical substrate or a lens 33 to be manufactured has a convex spherical surface 35 to be qualified. Lens 33 is arranged in the beam path of converging measuring light beam 21 such that surface 35 faces interferometer optics 14 and such that a center of curvature of convex surface 35 substantially coincides with crossover 23. Spherical wavefronts of measuring light beam 21 are reflected from surface 35 and travel back through interferometer optics 14 and are imaged on camera 31. On camera 31 the wavefronts reflected back from reference surface 25 and the wavefronts reflected back from surface 35 under test are superimposed and form interference fringes detected by camera 31. From a measurement of such interference fringes deviations of surface 35 from its target spherical shape may be determined. Based on such determination surface 35 may be machined for better conforming to its target shape.

An opening ratio k may be defined for surface 35 having a diameter D, a radius of curvature R and an opening angle α as $$k = \frac{1}{2\sin\alpha} = \frac{R}{D}, \qquad (1)$$

wherein D=2 R sinα for α<90°.

If surface 35 is an aspherical surface, the definition of equation 1 may be maintained by defining the radius R with respect to a best approximating sphere of the aspherical surface 35.

Figures 1, 2:
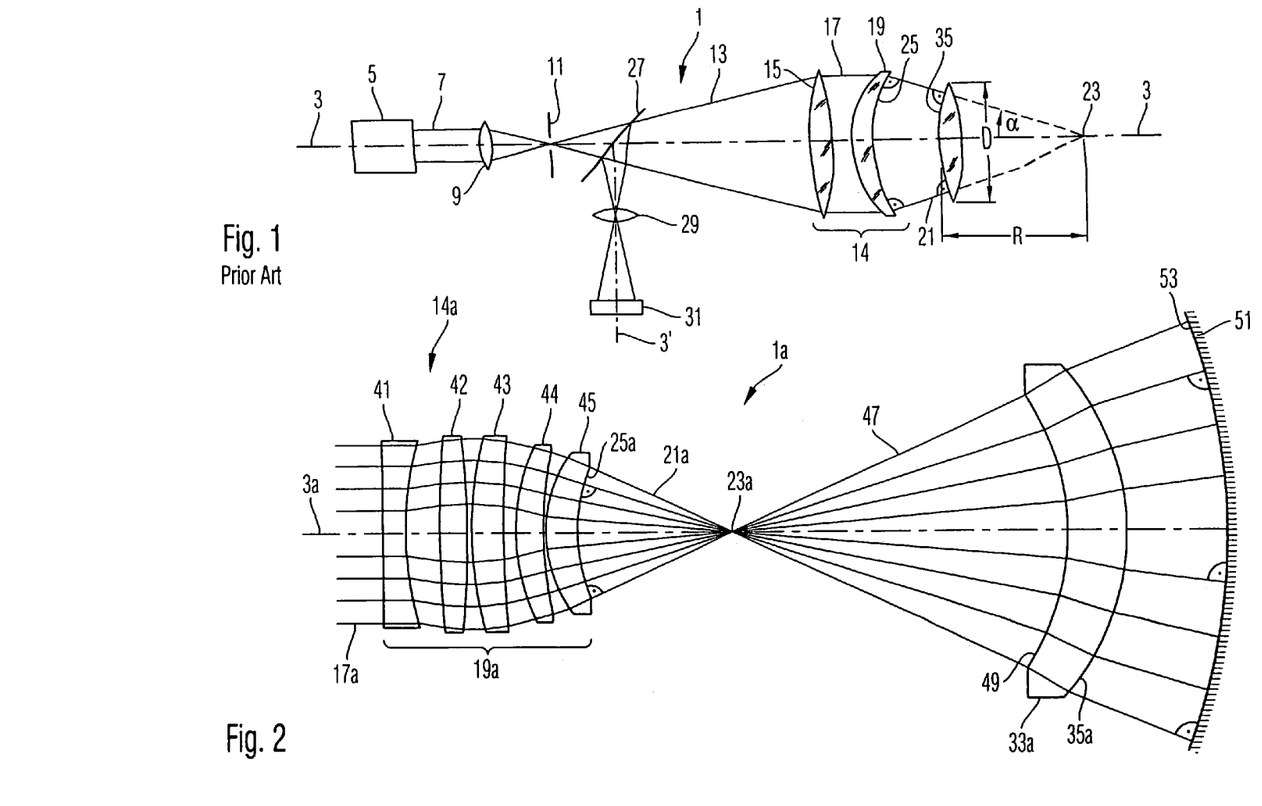
FIG. 1 illustrates a conventional interferometric apparatus and method.
FIG. 2 is a sectional view of a portion of an interferometer apparatus for performing a method according to a first embodiment of the invention.

It appears from FIG. 1, that for small values of the opening ratio k a diameter of lens 19 of interferometer optics 14 has to be substantially higher than diameter D of lens 33 under test. Manufacture of interferometer optics having a high diameter with the necessary precision is not only expensive but also demanding from its optical design.

SUMMARY OF THE INVENTION

The present invention has been accomplished taking the above problems into consideration.

Thus, it is an object of the present invention to provide an improved method for qualifying an optical surface.

It is also an object of the present invention to provide an improved method of manufacturing an optical surface.

It is a further object of the present invention to provide an interferometer apparatus and method suitable for qualifying convex optical surfaces with a high ratio of diameter over radius of curvature.

The forgoing objects are accomplished by providing a method of processing an optical substrate having a convex first surface by arranging the convex surface in a beam path of a measuring light beam of an interferometer where the measuring light beam is diverging and such that the convex surface faces away from the interferometer optics, wherein wavefronts of the measuring light beam having traversed the optical substrate are reflected back from a concave mirror, and wherein deviations of the convex surface from a target shape thereof are determined in dependence of an interferometrical measurement of the wavefronts reflected back from the concave mirror.

Thus, the convex surface is, in contrary to the prior art, arranged in a diverging portion of the measuring light beam which is formed after the same may have passed a corresponding crossover portion, rather than in a converging beam path of the measuring light beam. Forming a diverging beam of measuring light is possible with an interferometer optics having a comparatively small diameter. Even large diameter optical substrates may be qualified by using small diameter interferometer optics, accordingly.

This is accomplished by allowing the beam of measuring light to traverse the other surface of the optical substrate which other surface is different from the surface under test, i.e. the convex surface to be qualified. In the prior art method as illustrated with reference to FIG. 1 above, such other surface would not contribute to the measuring result.

According to an exemplary embodiment, the present invention provides a method of processing an optical substrate having a convex first surface and a second surface opposite the first surface, the method comprising: generating a diverging first measuring light beam using a first interferometer optics, the first measuring light beam having a portion of a beam path thereof where the first measuring light beam is a diverging beam; arranging the optical substrate in the first measuring light beam in the portion of the beam path thereof where the first measuring light beam is the diverging beam, with the second surface of the optical substrate facing towards the first interferometer optics; interferometrically taking a first measurement by superimposing first wavefronts generated by reflecting the first measuring light beam having passed the optical substrate from a mirror having a concave mirror surface, with second wavefronts not interacting with the first surface; determining deviations of the first surface of the optical substrate from a target shape thereof in dependence of the first measurement; and processing the first surface of the optical substrate in dependence of the determined deviations. The processing (e.g., machining) can comprise, for example, milling, grinding, loose abrasive grinding, polishing, ion beam etching, magneto-rheological figuring, or any combination thereof, or any suitable method for shaping the optical surface.

According to a further exemplary embodiment a compensating lens is arranged between the interferometer optics and the optical substrate for compensating a contribution of the second surface of the optical substrate. The compensating lens can be placed adjacent to the optical substrate (e.g., directly adjacent with no intervening lenses therebetween).

In some embodiments angles of incidence of light rays of the measuring light beam with respect to the second surface of the substrate or the surface of the calibrating lens are large and contribute to measuring errors.

According to a further exemplary embodiment it is then advantageous to provide a medium with a high refractive index in a gap between the surface of the compensating lens and the second surface of the substrate. The refractive index of such medium may be higher than 1.2, and it may be also higher than 1.5. Such medium may be formed by a liquid, such as water and oil or others.

The first measurement involves interferometrical detection of the first wavefronts generated by reflecting the measuring light beam from the concave mirror.

According to an exemplary embodiment, such first measurement also involves superimposing the first wavefronts with second wavefronts generated by reflecting the first measuring light beam from the first surface of the optical substrate. The concave mirror will then form a reference surface of the interferometer optics.

According to a further exemplary embodiment, wavefronts reflected from the first surface of the substrate do not substantially contribute to the measuring result. There is a further surface or reference surface provided in the interferometer apparatus for generating wavefronts for interference with the wavefronts reflected from the concave mirror in the first measurement.

The method of manufacturing the optical surface further includes processing of the optical surface after measuring the same, wherein the processing is performed in dependence of deviations of the measured optical surface from its target shape.

According to an exemplary embodiment, the method of manufacturing includes a final finishing of the machined optical surface.

The forgoing, and other features, and advantages of the invention will be more apparent from the following detailed description of preferred embodiments of the invention with reference to the accompanying drawings.

DETAILED DESCRIPTION OF EXEMPLARY EMBODIMENTS

In the exemplary embodiments described below, components that are alike in function and structure are designated as far as possible by like reference numerals. Therefore, to understand the features of the individual components of a specific embodiment, the descriptions of other embodiments should be referred to.

The embodiments of methods illustrated below involve interferometrically taking measurements of wavefronts generated by reflecting an incident beam provided by an interferometer apparatus from surfaces to be measured. Plural conventional interferometric methods may be used for taking such measurements. Examples of such interferometric methods are disclosed in e.g. U.S. Pat. No. 5,361,312, U.S. Pat. No. 5,982,490 and US 2002/0063867A1. The full disclosure of these patents and publications are incorporated herein by reference.

FIG. 2 illustrates a portion of an interferometer arrangement 1a used in a method for qualifying and manufacturing an optical substrate 33a having a convex surface 35a. The principal configuration of the interferometer arrangement 1a is similar to that shown in FIG. 1, and components thereof, such as light source, beam splitter, camera and others are not shown in FIG. 2.

A laser and further optics not shown in FIG. 2 are provided for supplying a parallel beam of measuring light 17a entering a focussing lens arrangement 19a of an interferometer optics 14a. Focussing lens arrangement 19a with lenses 41, 42, 43, 44 and 45 transforms parallel beam 17a into a converging beam 21a of measuring light forming a crossover in a region 23a. Lens 45 closest to crossover 23a has a concave lens surface 25a forming a reference surface or Fizeau surface of interferometer arrangement 1a. Wavefronts generated by reflecting measuring light from reference surface 25a are imaged on a detector as illustrated in FIG. 1 and not shown in FIG. 2.

After passing crossover 23a, the beam of measuring light is a diverging beam 47 in which wavefronts are substantially spherical wavefronts. The optical substrate to be qualified and manufactured is a lens 33a having a convex surface 35a and a concave surface 49. Convex surface 35a is the surface under test in the illustrated step of the qualifying procedure, i.e. deviations of the shape of surface 35a from a target shape thereof are to be determined with the method. Lens 33a is arranged in the diverging beam 47 of measuring light such that concave surface 49 faces towards interferometer optics 14a. Thus, wavefronts in the beam of measuring light 47 penetrate concave surface 49, travel through the substrate 33a and leave the substrate 33a through convex surface 35a for further being reflected back from a substantially spherical concave mirror surface 53 of a mirror 51.

The optical data of the optical elements shown in FIG. 2 are given in the following table 1:

The wavefronts of the measuring light reflected back from mirror surface 53 travel through substrate 33a and the interferometer optics 14a to interfere on the camera by superposition with the reference wavefronts reflected from reference surface 25a.

From an analysis of such interferometric measurement of wavefronts the surface shape of surface 35a and deviations of such surface shape from a target shape of surface 35a may be determined. Such analysis will involve knowledge of other optical parameters of lens 33a, such as a surface shape of concave surface 49, a refractive index of the material of lens 33a and a distance between surfaces 49 and 35a on optical axis 3a.

The distance between concave surface 49 and convex surface 35a may be mechanically determined, for instance. The surface shape of concave surface 49 may be determined by an interferometric method as illustrated with reference to FIG. 3. Such method uses an interferometer optics 14b which may be the same interferometer optics as used in FIG. 2 for determining the surface shape of convex surface 35a, or interferometer optics 14b may be different therefrom. Again, interferometer optics 14b has a reference surface 25b and forms a converging beam 21b of measuring light passing a crossover region 23b to form a diverging beam 47b of measuring light. Lens 33a is arranged in the diverging beam 47b such that concave surface 49 faces towards interferometer optics 14b and such that a center of curvature of surface 49 substantially coincides with crossover 23b. Wavefronts reflected back from concave surface 49 will coincide with wavefronts reflected back from reference surface 25b on a detector (not shown) of the interferometer arrangement such that the surface shape of concave surface 49 may be determined from a measuring result.

The images obtained from the detector in an interferometric measurement typically represent patterns of interference fringes which patterns are data processed by known methods to obtain maps of optical path differences (OPD). From such map of optical path differences a deviation d of the surface shape from a target shape thereof may be determined by the formula

TABLE 1

| ELEMENT | RADIUS OF CURVATURE | | THICKNESS | APERTURE DIAMETER | | GLASS |
|---|---|---|---|---|---|---|
| | FRONT | BACK | | FRONT | BACK | |
| 41 | 1361.0000 | 234.9600 | 17.0000 | 121.9030 | 121.2397 | SIO2 |
| | | | 16.7480 | | | Air |
| 42 | 732.8700 | −703.9000 | 18.0000 | 123.6002 | 124.7090 | SIO2 |
| | | | 2.0000 | | | Air |
| 43 | 215.0500 | 1150.0000 | 25.0000 | 125.3691 | 121.8868 | PBM2Y Ohara |
| | | | 5.0000 | | | Air |
| 44 | 130.0880 | 256.8300 | 20.0000 | 117.3549 | 110.9004 | PBM2Y Ohara |
| | | | 1.5000 | | | Air |
| 45 | 81.9850 | 112.1390 | 23.0000 | 102.8520 | 90.2425 | SIO2 |
| | | | 363.8024 | | | Air |
| 33a | −169.8698 | 161.8465 | 43.2000 | 194.3849 | 221.6199 | SIO2 |
| | | | 75.4020 | | | Air |
| 51 | −440.3000 | | | 290.2761 | | REFL |

$$d = \frac{OPD_{SinglePass}}{\frac{n}{\cos i} - \frac{1}{\sqrt{1 - n^2(1 - \cos^2 i)}}} \quad (2)$$

wherein n represents the refractive index of the substrate material of lens 33a;

i represents an angle of incidence of a light ray from the interior of lens 33a on surface 35a at each particular location; and $OPD_{SinglePass}$ represents the measured optical path difference at a single pass.

Figure 3:
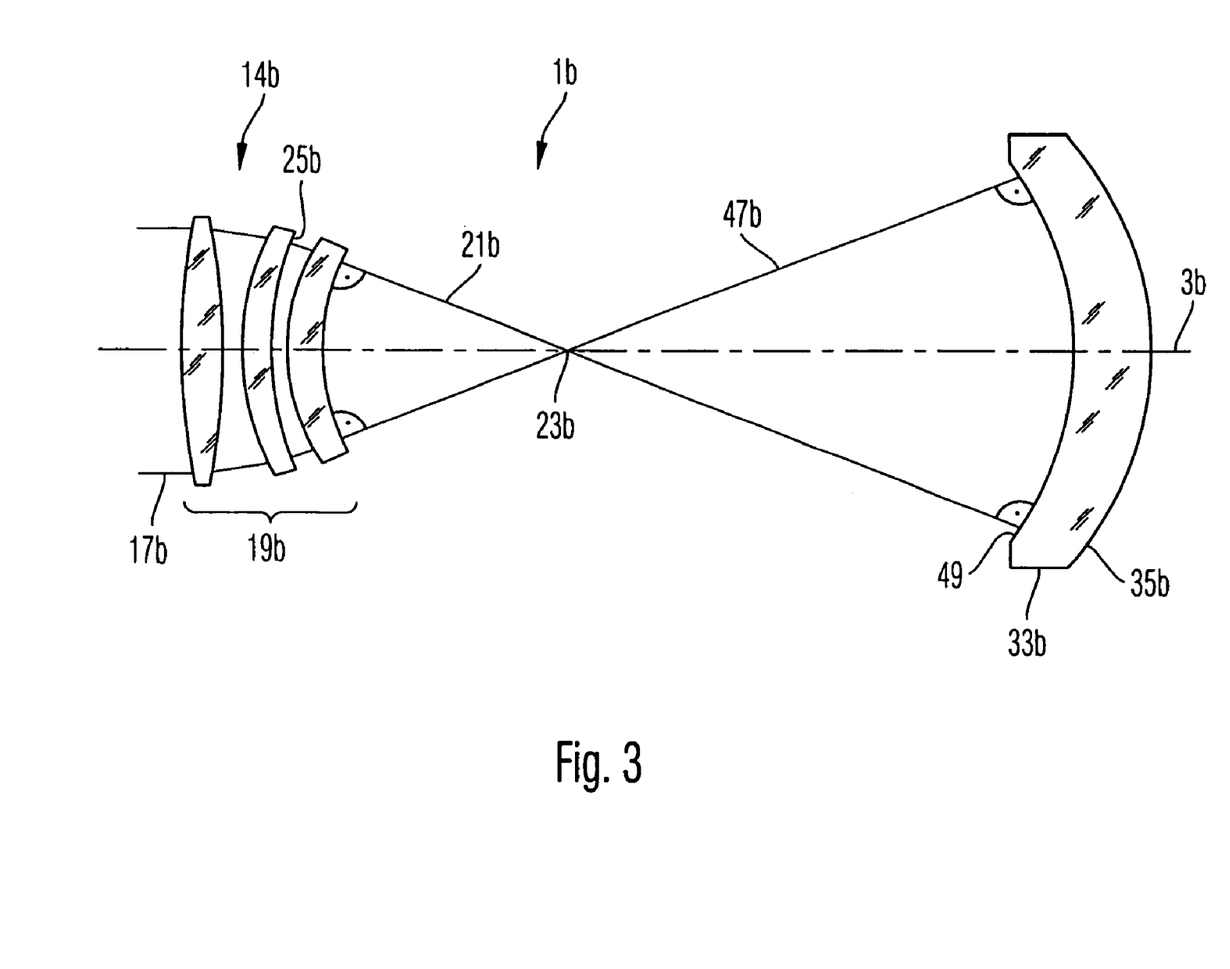
FIG. 3 is a sectional view of a portion of an auxiliary interferometer apparatus for performing the method according to the first embodiment of the invention.

From FIGS. 2 and 3 it appears that lens 33a having the convex surface 35a has a diameter which is larger than a diameter of lenses of interferometer optics 14a, 14b while it is still possible to determine the surface shape of lens surface 35a with a high accuracy.

Having qualified convex surface 35a it is then possible to identify those regions on surface 35a where deviations from the target shape thereof exceed a certain thresholds. A processing step (e.g., machining) is then performed to reduce these deviations and can comprise, for example, milling, grinding, loose abrasive grinding, polishing, ion beam etching, magneto-rheological figuring, or any combination thereof, or any suitable method for shaping the optical surface.

Thereafter, the measurement as illustrated in FIG. 2 is repeated to determine new deviations of surface 35a from its target surface. If these deviations still exceed the predetermined thresholds a further processing step is performed. Otherwise, a finishing step is performed on the optical surface 35a. The finishing may include a final polishing of the surface or depositing a suitable coating, such as a reflective coating, an anti-reflective coating, and a protective coating. A reflective coating may include, for example, a plurality of material layer pairs, for example 40 pairs of alternating molybdenum and silicon layers or other layers.

Thicknesses of such layers may be about 5 nm and will be adapted to a wavelength to be reflected from the optical surface, such that a reflective coefficient is substantially high. Finally, the reflective coating may be covered by a cap layer for passivating the reflective coating. The cap layer may include a layer formed by depositing ruthenium, for example.

An anti-reflective coating which is intended to reduce reflections of radiation from an interface of an optical element, such as a lens element, may include magnesium fluoride or lanthanum oxide or other conventional materials.

The above mentioned threshold value will differ from the application of the optical surface in the optical system for which it is designed. For example, if the optical surface is a lens surface in an objective for imaging a reticle structure onto a resist with radiation of a wavelength $\lambda$=193 nm, such threshold value may be in a range of about 2 nm to 10 nm, and if the optical surface will be used as a mirror surface in an imaging objective using EUV (extreme ultraviolet) radiation with a wavelength of e.g. $\lambda$=13.5 nm, the threshold value will be in a range of about 0.1 nm to 1.0 nm.

Figure 4:
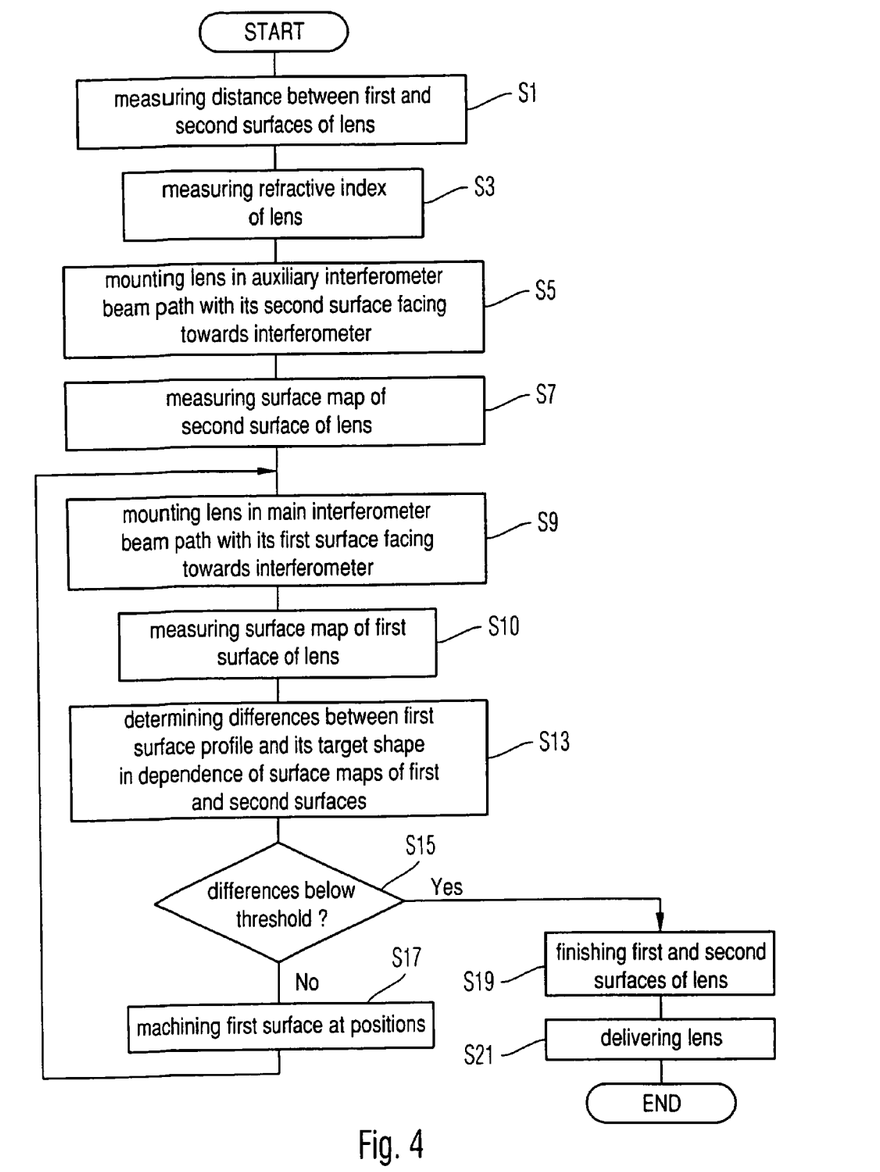
FIG. 4 is a flow chart of the method according to the first embodiment of the present invention.

The method of manufacturing the optical substrate, i.e. lens 33a, having the convex first surface 35a is summarized with reference to FIG. 4:

In a step S1 a center distance between concave surface 49 and convex surface 35a of lens 33a is determined by a conventional method. In a step S3 the refractive index of the lens material of lens 33a is determined by some conventional method. In a step S5 lens 33a is mounted in a beam path of an interferometer 1b as illustrated with reference to FIG. 3 above, i.e. such that a measurement of wavefronts generated by reflecting measuring light from concave surface 49 may be interferometrically performed. In a step S7 a map indicating deviations of surface 49 from its spherical shape is calculated.

In a step S9 lens 33a is mounted in a beam of measuring light as illustrated with reference to FIG. 2 above, i.e. lens 33a is mounted in diverging portion 47 of a beam of measuring light provided by interferometer optics 14a and such that wavefronts of diverging beam 47 are reflected from concave mirror surface 53 after traversing lens 33a.

From an analysis of the interferometric measuring results a surface map of convex surface 35a of lens 33a is determined in a step S11. In a step S13 differences between the surface shape of surface 35a and its target shape, i.e. a spherical shape, are determined from the surface map of concave surface 49 determined in step S7 and the surface map of convex surface 35a determined in step S11.

In a decision step S15 it is then determined whether the differences determined in step S13 are below a predetermined threshold. If not, the convex surface 35 is machined in a step S17 to reduce these differences, and the method is continued with step S9, i.e. mounting the lens 33a in the interferometer beam path again and repeating steps S9 to S15. If the differences are below the threshold, the lens 33a, including its convex surface 35a, undergo a finishing procedure in a step S19 and the lens is delivered in a step S21.

It is to be noted that it is not necessary that the above-mentioned threshold is a constant threshold over the whole area of the optical surface. It is possible that the threshold is dependent on e.g. a distance from a center of the surface or some other parameters.

Figure 5:
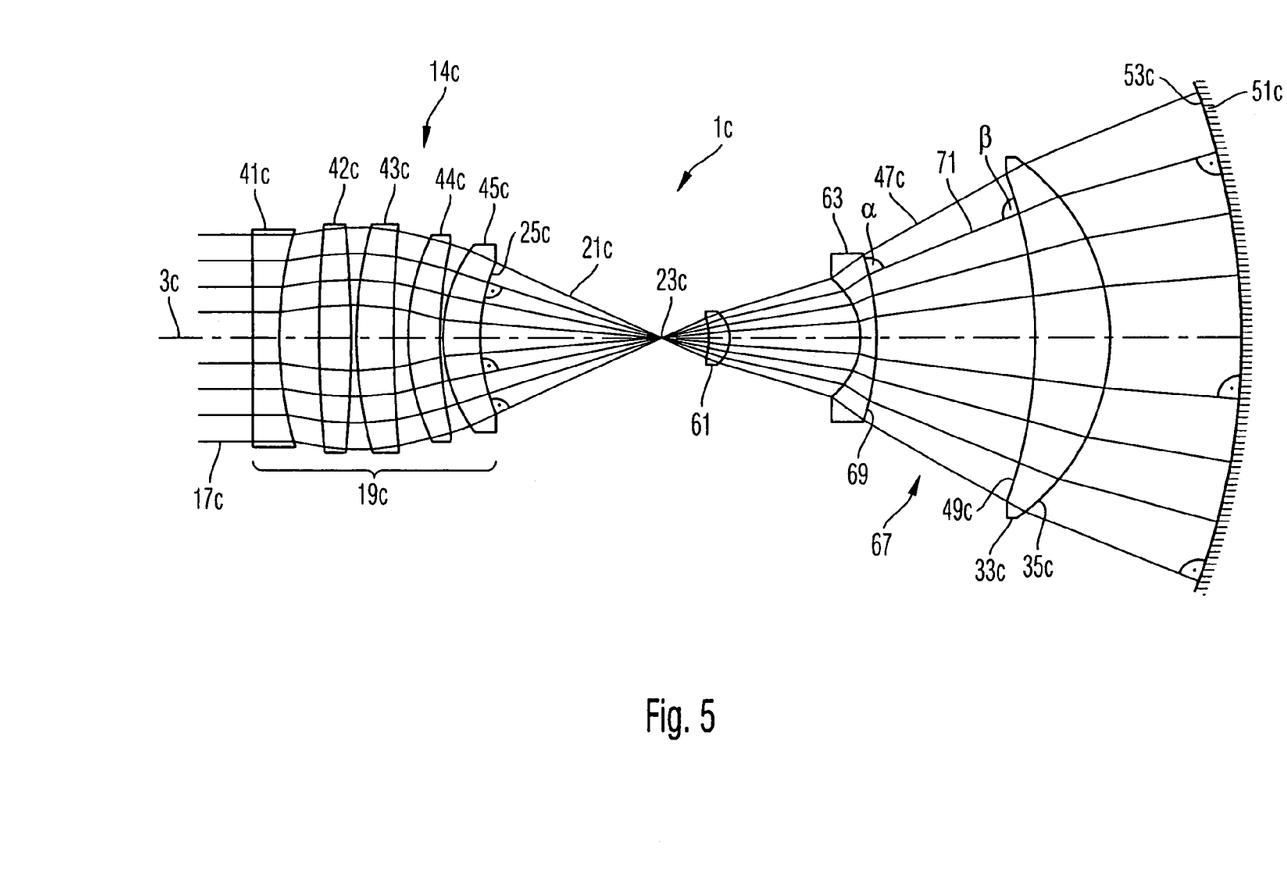
FIG. 5 is a sectional view of a portion of an interferometer apparatus used for performing a method according to a second embodiment of the present invention.

FIG. 5 illustrates an embodiment of the method of qualifying convex surface 35 of lens 33 with an interferometer arrangement 1c which is similar to that illustrated above with reference to FIG. 2. Lens 33c to be manufactured is arranged in a diverging beam 47c of measuring light such that surface under test 35c faces away from an interferometer optics 14c. Interferometer optics 14c generates a converging beam 21c of measuring light forming a crossover region 23c. Wavefronts of the diverging beam 47c having traversed lens 33c are reflected back from a mirror 51c having a concave substantially spherical mirror surface 53c such that the measuring light is orthogonally incident on mirror surface 53c. To achieve such normal incidence, compensating lenses 61 and 63 are arranged in the beam path of diverging beam 47c between crossover 23c and lens 33c. The shapes of surfaces of lenses 61 and 63 and their position in the diverging beam 47 are determined such that lenses 61, 63 and 33 together have an influence on the diverging beam such that the normal incidence condition on spherical mirror surface 35 is fulfilled.

The optical data of the optical elements shown in FIG. 5 are given in the following table 2:

TABLE 2

| ELEMENT | RADIUS OF CURVATURE | | THICKNESS | APERTURE DIAMETER | | GLASS |
| --- | --- | --- | --- | --- | --- | --- |
| | FRONT | BACK | | FRONT | BACK | |
| 41c | 1361.0627 | 234.9588 | 17.0000 | 150.0636 | 149.1261 | 'sio633' |
| | | | 16.6990 | | | Air |
| 42c | 732.9000 | −703.9245 | 18.0000 | 151.3565 | 152.4830 | 'sio633' |
| | | | 2.0000 | | | Air |
| 43c | 215.0580 | 1150.0314 | 25.0000 | 153.8205 | 150.5385 | 'Pbm2y' |
| | | | 5.0000 | | | Air |
| 44c | 130.0915 | 256.8367 | 20.0000 | 142.8727 | 137.4814 | 'Pbm2y' |
| | | | 1.5125 | | | Air |
| 45c | 81.9864 | 112.1422 | 23.0000 | 122.6959 | 111.1309 | 'sio633' |
| | | | 132.7463 | | | Air |
| 61 | −36.7918 | −20.2423 | 12.0384 | 21.6052 | 28.8372 | 'Bk7' |
| | | | 95.0900 | | | Air |
| 63 | −44.0306 | −177.8219 | 9.0010 | 70.7640 | 93.3427 | 'Bk7' |
| | | | 90.8770 | | | Air |
| 33c | −259.4900 | −129.573 | 46.0000 | 203.9505 | 221.6199 | 'sio633' |
| | | | 75.3492 | | | Air |
| 51c | −440.3302 | | | 291.3235 | | REFL |

Figure 6:
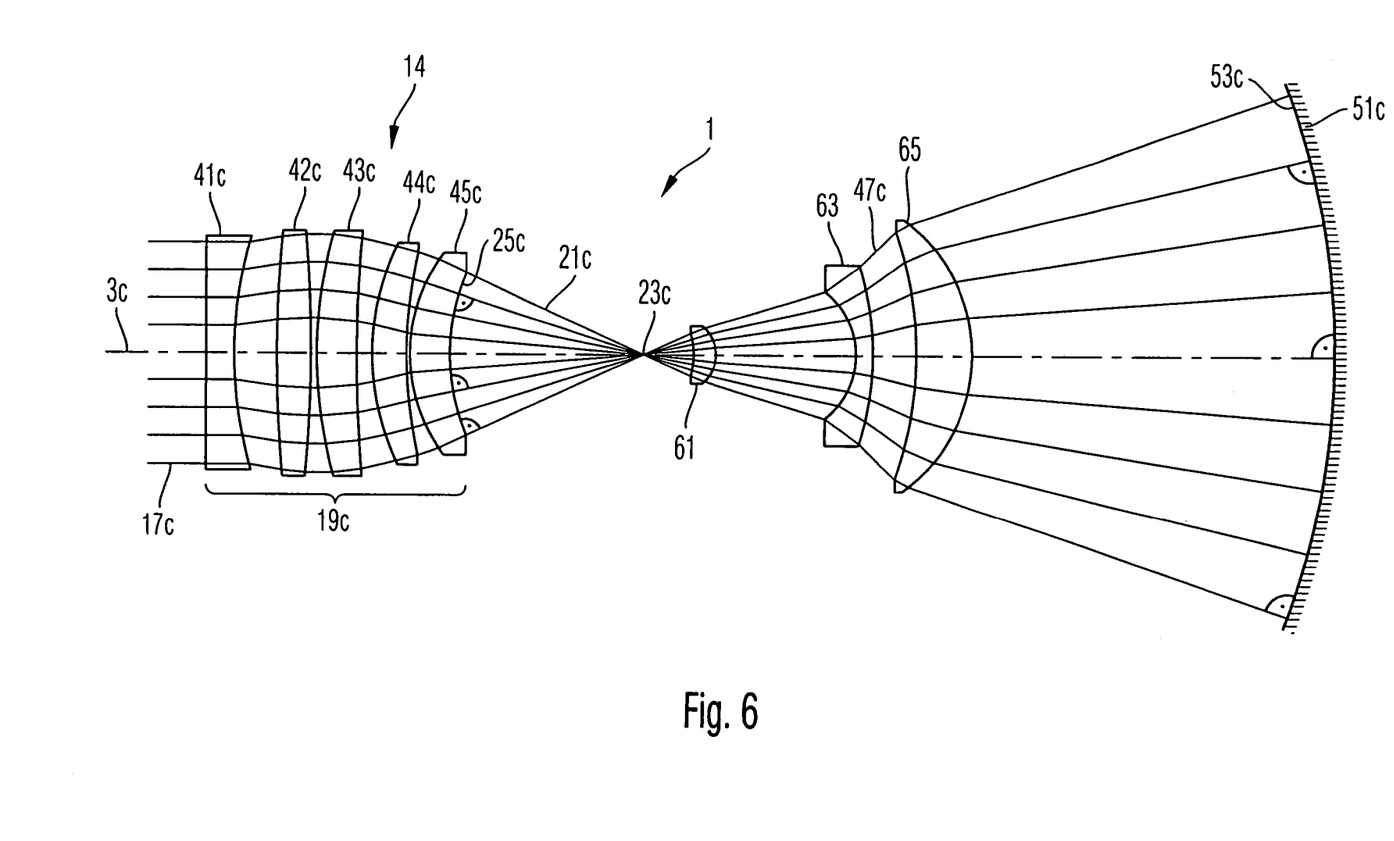
FIG. 6 is a sectional view of a further interferometer arrangement used for calibrating an interferometer optics in the method according to the second embodiment.

A method of calibrating the interferometer arrangement shown in FIG. 5 is illustrated in FIG. 6. For calibrating the interferometer arrangement lens 33c to be qualified is removed from the diverging beam 47c of measuring light, and a calibrating lens 65 is arranged therein. Calibrating lens 65 has a diameter which is smaller than a diameter of lens 33c, and lens 65 has surfaces manufactured with a high precision to such shape that compensating lenses 61 and 63 and calibrating lens 65 together influence the diverging beam 47 such that it is substantially orthogonally incident on mirror surface 53c. An interferometric measurement of wavefronts reflected back from reference surface 25c of the interferometer optics 14c interfering with wavefronts reflected back from mirror 53c is used to calibrate interferometer optics 14c and compensating lenses 61 and 63.

The optical data of the optical elements shown in FIG. 6 are given in the following table 3:

indicates an angle of incidence of ray 71 with respect to concave surface 49c of lens 33c. The angles of incidence α and β are substantially different from 90° and require a very precise positioning of lenses 63 and 33c relative to each other. In particular, a predetermined distance between lenses 63 and 33c along optical axis 3c has to be carefully maintained. Otherwise the desired normal incidence of measuring light on mirror surface 53c will not be fulfilled.

Figure 7:
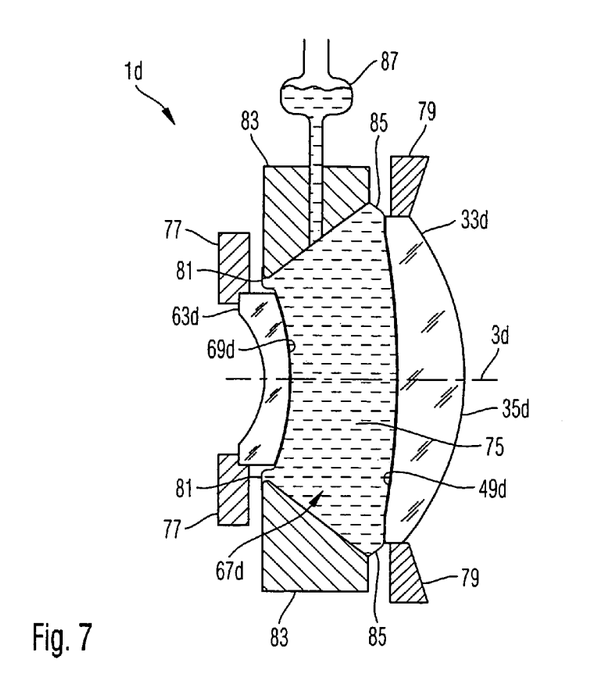
FIG. 7 is a sectional view of a portion of an apparatus used in a method according to a third embodiment of the present invention.

FIG. 7 illustrates an embodiment where the angles of incidence α and β shown in FIG. 5 are closer to 90° such that demands on relative positions of optical elements in the interferometer arrangement 1d are relaxed. A liquid medium 75 is provided in a gap 67d between a compensating lens 63d and a lens 33d to be manufactured. The liquid medium is an oil having an index of refraction of n=1.45. Compared to FIG. 5 where the medium in gap 67 is air, the refractive

TABLE 3

| ELEMENT | RADIUS OF CURVATURE | | THICKNESS | APERTURE DIAMETER | | GLASS |
| --- | --- | --- | --- | --- | --- | --- |
| | FRONT | BACK | | FRONT | BACK | |
| 41c | 1361.0627 | 234.9588 | 17.0000 | 150.0636 | 149.1261 | 'sio633' |
| | | | 16.6990 | | | Air |
| 42c | 732.9000 | −703.9245 | 18.0000 | 151.3565 | 152.4830 | 'sio633' |
| | | | 2.0000 | | | Air |
| 43c | 215.0580 | 1150.0314 | 25.0000 | 153.8205 | 150.5385 | 'Pbm2y' |
| | | | 5.0000 | | | Air |
| 44c | 130.0915 | 256.8367 | 20.0000 | 142.8727 | 137.4814 | 'Pbm2y' |
| | | | 1.5125 | | | Air |
| 45c | 81.9864 | 112.1422 | 23.0000 | 122.6959 | 111.1309 | 'sio633' |
| | | | 132.7465 | | | Air |
| 61 | −36.7918 | −20.2423 | 12.0384 | 21.6052 | 28.8372 | 'Bk7' |
| | | | 95.0900 | | | Air |
| 63 | −44.0306 | −177.8219 | 9.0010 | 70.9200 | 93.6581 | 'Bk7' |
| | | | 24.0507 | | | Air |
| 65 | −273.3461 | −92.3903 | 32.2757 | 126.9652 | 221.6199 | 'sio633' |
| | | | 214.5535 | | | Air |
| 51c | −440.3302 | | | 291.7492 | | REFL |

In the following reference is made to FIG. 5 again. A gap 67 is formed between concave surface 49c of lens 33c under test and a surface 69 of compensating lens 63. In FIG. 5, α indicates an angle of incidence of a ray 71 of beam 47 with respect to surface 69 of compensating lens 63, and β index of the oil is substantially higher and closer to that of lenses 63d and 33d such that the angles of incidence will be closer to 90°.

In FIG. 7 mounting frames for lenses 63d and 33d are indicated with reference numerals 77 and 79, respectively.

A flexible foil 81 is provided for preventing direct contact of liquid 75 with surface 69*d* of lens 63*d*. Foil 81 is attached to a ring shaped frame 83 defining a space in which liquid 75 is contained.

Further, a flexible foil 85 is provided for preventing a direct contact of liquid 75 with surface 49*d* of lens 33*d*, wherein foil 85 is also attached to ring shaped frame 83. Thus, foils 81 and 85 and frame 83 form a container for the liquid 75 filling the gap 67 between surfaces 69*d* and 49*d* of lenses 63*d* and 33*d*, respectively. A reservoir 87 for liquid 75 is arranged above frame 83 to insure a sufficient liquid pressure within gap 67 such that foils 81 and 85 are pressed into intimate contact with lens surfaces 69*d* and 49*d*.

Figure 8:
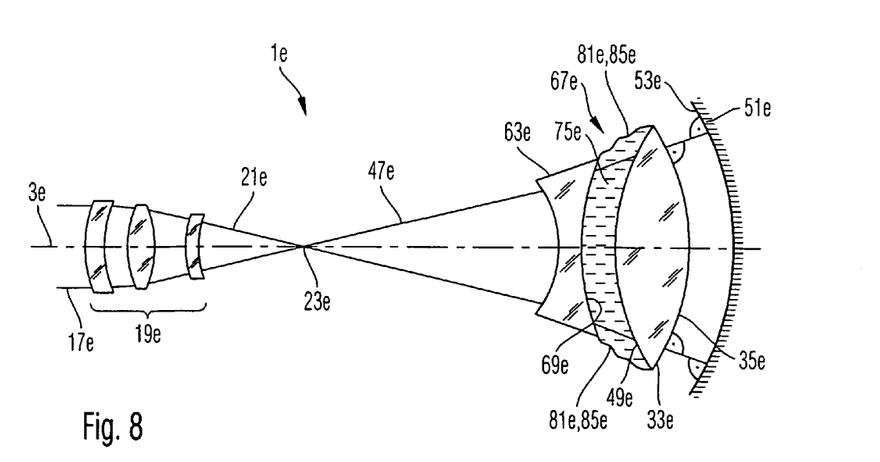
FIG. 8 is a sectional view of a portion of an interferometer apparatus used in a method according to a fourth embodiment of the present invention.

FIG. 8 illustrates a further embodiment of an interferometer arrangement 1*e* and method for qualifying a convex spherical surface 35*e* of a lens 33*e*, wherein a liquid 75*e* is filled in a gap 67*e* formed between a surface 69*e* of a compensating lens 63*e* and a surface 49*e* of lens 33*e*. Again, a focussing arrangement 19*e* is provided for transforming a parallel beam 17*e* into a converging beam 21*e* of measuring light forming a crossover at a region 23*e*. Downstream thereof, the beam of measuring light is a diverging beam 47*e* traversing compensating lens 63*e*, liquid medium 75*e* and lens 33*e* with its surface 35*e* under test such that wavefronts of the measuring light are reflected back from a concave spherical mirror surface 53*e* of a mirror 51*e*. Rays of the beam of measuring light are substantially normally incident both on surface 35*e* under test and on mirror surface 53*e*. Mirror surface 53*e* is a reference surface calibrated independently by some other conventional method known to the person skilled in the art. From an interferometric measurement of wavefronts reflected back from reference mirror surface 53*e* and wavefronts reflected back from surface 35*e* under test, deviations of the surface shape of surface 35*e* from a target shape thereof may be determined. Again, the presence of liquid medium 75*e* in gap 67*e* relaxes requirements on a positioning of lenses 63*e* and 33*e* with respect to mirror 51*e* for fulfilling the desired normal incidence condition of the measuring light on mirror surface 53*e*.

Mounting frames for lenses 63*e* and 33*e* and for foils 81*e* and 85*e* forming a container for liquid 75 are not shown in FIG. 8.

Figure 9:
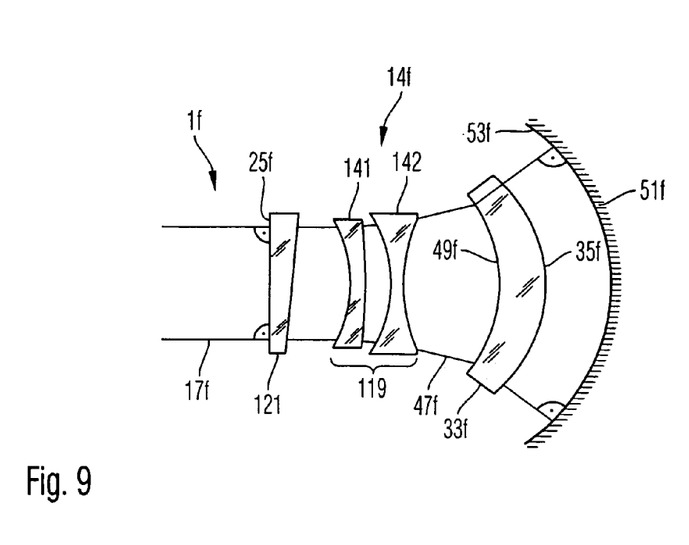
FIG. 9 is a schematic view of a portion of an interferometer apparatus used in a method according to a fifth embodiment of the present invention.

FIG. 9 schematically illustrates a further embodiment of an interferometer apparatus 1*f* for testing a convex surface 35*f* of a lens 33*f*. In the embodiment shown in FIG. 9, an interferometer optics 14*f* comprises a diverging lens arrangement 119 having plural lenses 141, 142 for generating a diverging beam 47*f* of measuring light directly, without forming a crossover region (reference numeral 23*a* in FIG. 2). A reference surface or Fizeau surface 25*f* is provided on a wedge shaped plate 121 disposed in a parallel beam 17*f*.

Figure 10:
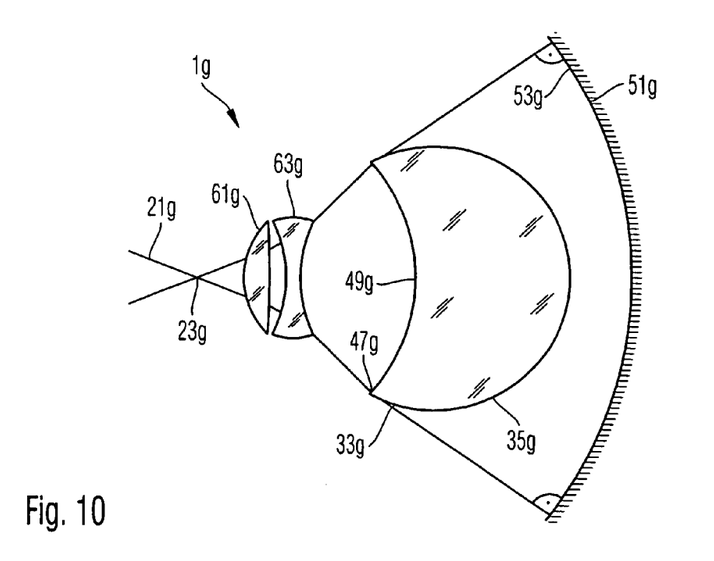
FIG. 10 is a schematic view of a portion of an interferometer apparatus used in a method according to an sixth embodiment of the present invention.

FIG. 10 schematically illustrates a further embodiment of an interferometer apparatus 1*g* for testing a convex surface 35*g* of a lens 33*g*. An interferometer optics (not shown in FIG. 10) generates a converging beam 21*g* forming a diverging beam downstream of a crossover region 23*g*.

Compensating lenses 61*g* and 63*g* are disposed in this diverging beam 23*g*, generating a stronger diverging beam 47*g*. Beam 47*g* traverses the optical element 33*g* to be tested and is reflected under normal incidence from a spherical surface 53*g* of a mirror 51*g*. The optical element 33*g* to be tested has a concave surface 49*g* facing towards the interferometer optics, and a convex surface 35*g* facing towards mirror 51. Convex surface 35*g* has a particularly low opening ratio k since surface 35*g* has an opening angle α (see equation 1) of more than 90 degrees.

It is a particular advantage of the invention that it allows to test convex surfaces having opening angles of more than 90 degrees.

In the above illustrated embodiments the convex surface under test is a substantially spherical surface, and the concave mirror surface 53 from which the measuring light having traversed the lens and surface under test is reflected is a substantially spherical mirror surface. However, the invention is not limited to such embodiments. It is evident that the inventive concept may be also applied to measuring lenses having a convex aspherical surface which may be arranged in the beam path of measuring light in a same way as shown in FIGS. 2, 5, 7 to 10.

Further, depending on the application, both for spherical and aspherical convex surfaces under test the concave mirror may have a spherical or aspherical shape.

In the above illustrated embodiments the interferometer arrangement is a Fizeau-type interferometer. It is to be noted, however, that the invention is not limited to such type of interferometer. Any other type of interferometer, such as a Twyman-Green-type of interferometer, a Michelson-type interferometer and any other suitable type of interferometer may be used.

In the above, where maps of surface errors are determined by an interferometric measurement any method for interferogram evaluation may be used. Possible applicable methods are disclosed in the book edited by Daniel Malacara, Optical Shop Testing, 2nd edition, Wiley interscience Publication (1992). Further, methods of phase shifting interferometry (PSI) may be applied, wherein a plurality of interferograms are analyzed for producing a surface map. Examples of phase shifting interferometry are also presented in the book mentioned above by Malacara. The phase shift is advantageously generated by varying the wavelength of the light providing the interferometric measuring beam using a wavelength tuneable light source.

It is further to be noted that the optical components involved in the above interferometric methods are subject to gravity during measurement. This may result in deformations of the surfaces of those components which are fixed in suitable mounts for arranging the components within the beam path of the interferometer. Even though the optical axis is oriented horizontally in FIGS. 1 to 3 and 5 to 10, it is also possible to perform the same measurements with an optical axis oriented vertically in the gravitational field. In any event, it is possible to use mathematical methods to simulate deformations of the optical components in the gravitational field. One such method is known as FEM ("finite element method"). All determinations of optical properties and deviations illustrated above may involve taking into account results of such mathematical methods for correcting and/or improving the determined results.

The present invention has been described by way of exemplary embodiments to which it is not limited. Variations and modifications will occur to those skilled in the art without departing from the scope of the present invention as recited in the appended claims and equivalents thereof.

What is claimed is:

1. A method of processing an optical substrate having a convex first surface and a second surface opposite the first surface, the method comprising:

generating a diverging first measuring light beam using a first interferometer optics, the first measuring light beam having a portion of a beam path thereof where the first measuring light beam is a diverging beam;

arranging the optical substrate in the first measuring light beam in the portion of the beam path thereof where the first measuring light beam is the diverging beam, with the second surface of the optical substrate facing towards the first interferometer optics;

interferometrically taking a first measurement by superimposing first wavefronts generated by the first measuring light beam having traversed the optical substrate with second wavefronts not interacting with the first surface;

determining deviations of the first surface of the optical substrate from a target shape thereof in dependence on the first measurement; and processing the first surface of the optical substrate in dependence on the determined deviations.

2. The method according to claim 1, further comprising arranging at least one compensating lens in the first measuring light beam between the interferometer optics and the optical substrate.

3. The method according to claim 2, wherein the at least one compensating lens is positioned in the portion of the beam path thereof where the first measuring light beam is the diverging beam.

4. The method according to claim 2, wherein the at least one compensating lens comprises a first compensating lens adjacent to the optical substrate, wherein a gap is formed between a surface of the first compensating lens and the second surface of the optical substrate, and wherein a medium is arranged in the gap, the medium having a refractive index higher than 1.2.

5. The method according to claim 4, wherein the medium comprises a liquid.

6. The method according to claim 5, wherein a flexible foil is provided between the liquid and at least one of the surface of the first compensating lens and the second surface of the optical substrate.

7. The method according to claim 1, wherein the second wavefronts are generated by reflecting one of a portion of the first measuring light beam and a source beam from which the first measuring light beam is formed, from a reference surface.

8. The method according to claim 1, wherein the second wavefronts are generated by reflecting a portion of the first measuring light beam from the first surface of the optical substrate.

9. The method according to claim 1, further comprising:
arranging a calibrating lens in the first measuring light beam, while the optical substrate is not arranged in the beam path of the first measuring light beam; and
interferometrically taking a second measurement by superimposing third wavefronts generated by the first measuring light beam having traversed the calibrating lens with the second wavefronts;
wherein the deviations of the first surface of the optical substrate from its target shape are determined in dependence on the first measurement and the second measurement.

10. The method according to claim 9, wherein the first measurement is taken by superimposing the first wavefronts with reference wavefronts, and wherein the second measurement is taken by superimposing the third wavefronts with the reference wavefronts.

11. The method according to claim 1, further comprising:
generating a second measuring light beam using a second interferometer optics;
arranging the optical substrate in the second measuring light beam with the second surface of the optical substrate facing towards the second interferometer optics;
interferometrically taking a third measurement of fourth wavefronts generated by reflecting the second measuring light beam from the second surface of the optical substrate;
wherein the deviations of the first surface of the optical substrate from its target shape are determined in dependence on the first measurement and the third measurement.

12. The method according to claim 1, wherein the processing of the first surface is only performed if the deviations exceed a predetermined threshold.

13. The method according to claim 1, wherein the determining of deviations and the processing of the first surface are repeatedly performed.

14. The method according to claim 1, further comprising finishing the first surface of the optical substrate.

15. The method according to claim 14, wherein the finishing comprises applying a coating to the first surface of the optical substrate.

16. The method according to claim 15, wherein the coating comprises at least one of a reflective coating, an anti-reflective coating and a protective coating.

17. The method according to claim 1, wherein a ratio of a radius of curvature of the first surface to a diameter of the optical substrate is less than 2.5.

18. The method according to claim 1, wherein a ratio of a radius of curvature of the first surface to a diameter of the optical substrate is higher than 0.5.

19. The method according to claim 1, wherein the first surface has an opening angle of more than 90°.

20. An optical system comprising a plurality of lenses, wherein at least one lens of the plurality of lenses is an optical substrate manufactured by the method according to any of claims 1–19.

21. A method of manufacturing an optical system, comprising:
processing an optical substrate by the method according to any of claims 1—20;
and arranging the optical substrate with one or more lenses to form an optical system.

22. The method according to claim 21, wherein the first surface has an opening ratio smaller than an opening ratio of the concave mirror surface.

* * * * *